United States Patent [19]

Christy

[11] 4,018,830
[45] Apr. 19, 1977

[54] PHENYLTHIOARALKYLAMINES

[75] Inventor: Marcia Elizabeth Christy, Perkasie, Pa.

[73] Assignee: Merck & Co., Inc., Rahway, N.J.

[22] Filed: Nov. 25, 1974

[21] Appl. No.: 526,984

Related U.S. Application Data

[63] Continuation of Ser. No. 860,076, Sept. 22, 1969, abandoned.

[52] U.S. Cl. .................. 260/570.9; 260/243 B; 260/247.1 R; 260/268 R; 260/268 C; 260/293.73; 260/501.21; 260/516; 260/544 N; 260/558 S; 260/562 P; 424/246; 424/248; 424/250; 424/267; 424/316; 424/330; 424/248.52
[51] Int. Cl.$^2$ .......................... C07C 97/28
[58] Field of Search ............. 260/570.9, 501.21

[56] References Cited

UNITED STATES PATENTS 3,812,177  5/1974  Engelhardt et al. ........ 260/570.9 X

OTHER PUBLICATIONS

Knabe et al., "Archiv der Pharmazie", vol. 295, No. 9, pp. 690–697, (1962).
Its, "Chemical Abstracts", vol. 52, pp. 9005–9006, (1958).

*Primary Examiner*—Robert V. Hines
*Attorney, Agent, or Firm*—Daniel T. Szura; J. Jerome Behan

[57] ABSTRACT

Phenylthioaralkylamines and 2-phenylthiobenzylamines are prepared by reaction of the corresponding phenylthiobenzoyl chloride or homologs thereof with ammonia or an amine to produce the corresponding phenylthiobenzamide or N-substituted or N,N-disubstituted derivative thereof followed by reduction with lithium aluminum hydride to produce the corresponding phenylthiobenzylamine or the N-substituted or N,N-disubstituted derivative thereof. The compounds are also prepared by reaction of the corresponding phenylthiobenzyl halide with ammonia or a selected amine. The compounds are active as antiarrhythmics.

3 Claims, No Drawings

PHENYLTHIOARALKYLAMINES

This application is a continuation of co-pending application Ser. No. 860,076 filed Sept. 22, 1969 and now abandoned.

This invention relates to arylthioaralkylamines and derivatives thereof. More specifically, it relates to certain substituted and unsubstituted phenylthioaralkylamines and the corresponding N-substituted derivatives thereof such as the N-heterocyclic, the N-alkyl and the N,N-dialkyl derivatives thereof.

This invention also relates to the novel processes and the novel intermediates utilized in the production of new phenylthioaralkylamines, to pharmaceutical formulations of the new aralkylamines and to methods of treating or preventing cardiac arrhythmias using the novel compounds, and/or pharmaceutical formulations thereof, described herinafter.

The new compounds of our invention are unsymmetrical thio ethers in which one of the two substituents is an aromatic ring having at least one of its hydrogens replaced by a straight or branched chaim amino alkyl radical, or an amino heterocyclic radical and in which the other substituent is a homocyclic or heterocyclic ring selected from aryl, substituted aryl, heterocyclic and substituted heterocyclic substituents. The compounds of my invention are represented structurally as follows:

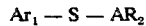

in which $Ar_1$ is a phenylalkyl amine substituent and $Ar_2$ is a substituted or unsubstituted homocyclic or heterocyclic ring of from 5 to 6 atoms, such as an aromatic ring, a heteroaromatic ring or a partially or completely reduced aromatic or heteroaromatic ring or a partially or completely reduced aromatic or heteroaromatic ring.

A preferred class of compounds of my invention are represented structurally as arylthioaralkylamines of the formula

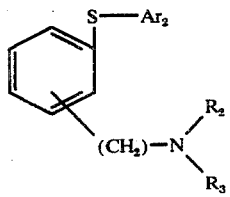

in which $m$ is an integer varying from 1 to 4 inclusive; $R_2$ and $R_3$ are either similar or dissimilar and are either hydrogen, alkyl (preferably of from 1 to 6 carbon atoms), branched chain alkyl, alkenyl, alkynyl (each preferably containing 1 to 6 carbon atoms), and can be joined together or alternatively may be linked through an atom of carbon, nitrogen, oxygen, or sulfur to one of the methylene substituents bridging the aromatic ring and the amine radical to form a heterocyclic ring of from 5 to 6 atoms such as 1-piperidyl, 1-pyrrolidinyl, 1-morpholinyl, 4-thiomorpholinyl, or 1-loweralkyl-4-piperazinyl and $Ar_2$ is aryl, especially phenyl or substituted phenyl, heterocyclic aromatic or a partially or completely reduced derivative thereof.

Also included within the scope of my invention are derivatives of compounds having the above formula in which one or more of the aryl or heterocyclic rings, or one of the reduced derivatives is further substituted.

A preferred group of such compounds includes derivatives in which one or more of the hydrogens of the phenyl ring and/or one or more of the hydrogens of the ring represented by $Ar_2$ is replaced by substituents selected from the group consisting of hydrogen, an alkyl group having up to 6 carbon atoms, an alkenyl group having up to 6 carbon atoms, a perfluoroalkyl group having up to 4 carbon atoms, a phenyl or a substituted phenyl radical, amino, an alkylamino group having up to 4 carbon atoms, a dialkylamino group having up to 8 carbon atoms, an alkylsulfonylamino group having up to 4 carbon atoms, halogen (fluorine, chlorine, bromine, or iodine), hydroxyl, an alkoxyl group having up to 4 carbon atoms, a perfluoroalkoxyl group having up to 4 carbon atoms, a perfluoroalkoxyl group having up to 4 carbon atoms, mercapto, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms. More than one of these substituents may be on each ring.

An especially preferred group of compounds included within the scope of my invention is represented by the formula:

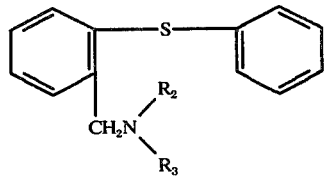

in which $R_2$ and $R_3$ are either hydrogen, alkyl (preferably of from 1 to 6 carbon atoms), alkenyl, alkynyl (each preferably of from 1 to 6 carbon atoms), and can be joined together through an atom of carbon, nitrogen, oxygen or sulfur to form a heterocyclic ring of from 5–6 atoms (such as 1-piperidyl, 1-pyrrolidinyl, 4-morpholinyl, 4-thiomorpholinyl of 1-loweralkyl-4-piperazinyl).

Illustrative of the compounds included within the scope of my invention are 2-phenylthiobenzylamine, 3-phenylthiobenzylamine, 4-phenylthiobenzylamine, the corresponding secondary amines as for example the N-methyl, N-ethyl, N-propyl, N-allyl, N-propargyl, N-isopropyl, N-butyl, N-t-butyl, N-amyl and the N-acyl derivatives thereof as well as the corresponding N,N-dialkyl derivatives thereof.

The compounds represented above, in either their free base or salt form, possess useful pharmacological properties. In particular, they have been found to possess antiarrhythmic activity. It has been found that the administration of compounds of the present invention, depicted in the above formula, results in the prevention of arrhythmia in animals under conditions which ordinarily cause the development of arrhythmia in the animal 100% of the time.

It has further been found that administration of the compounds of the present invention will arrest an existing arrhythmia in the animal being treated and cause a resumption of normal cardiac rhythm. As antiarrythmic agents, these compounds may be administered orally or parenterally. The formulations for administration may be prepared in conventional manner, employing conventional pharmaceutical carriers and excipients.

The non-toxic acid addition salts useful as components in the compositions provided by the present invention are salts formed by the reaction of an equivalent amount of the amine compound of the above formula and an acid which is pharmacologically acceptable in the intended doses. Salts of the above compound which are useful are salts of the amine with hydrochloric acid, hydrobromic acid, sulfuric acid, phosphoric acid, fumaric acid, acetic acid, propionic acid, lactic acid, gluconic acid, maleic acid, succinic acid, tartaric acid, and the like. Salts of these acids with the amine base are useful as the active component of the compositions in the method of this invention.

The daily doses are based on the total body weight of the test animal and vary between about 1.00 and 100.00 mg./kg. for mature animals. Thus, a unit dose based on four-times-a-day administration is between 2.5 mg. and 250 mg. for a 10 kg. dog, and a total daily dose for a 10 kg. dog would vary between about 10 mg. and 1,000 mg. For larger animals, up to 100 kg. and above, proportional dosages are employed, based on the weight of the animal. Suitable dosage units provided for the administration of the compositions used in the method of the invention are tablets, capsules (which may be suitably formulated for either immediate or sustained release), syrups, elixirs, parenteral solutions, and the like. These dosage forms preferably contain per unit one or more multiples of the desired dosage unit in combination with the pharmaceutically acceptable diluent or carrier required for preparing the dosage unit.

The compounds represented by the above structural formulas may be prepared as illustrated below.

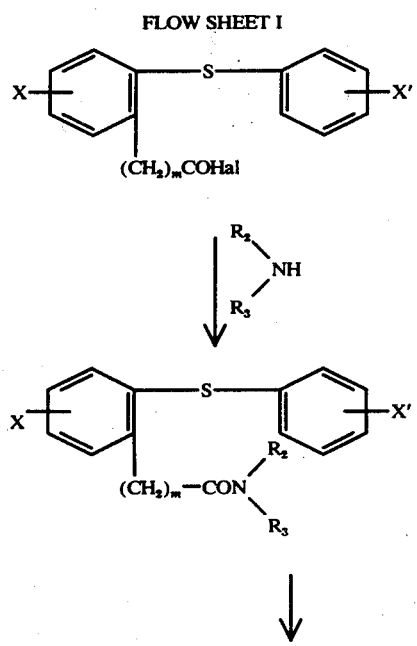

FLOW SHEET I

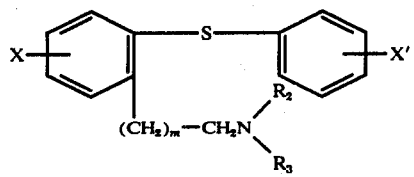

-continued wherein
Hal is halogen especially chlorine or bromine;
$R_2$ and $R_3$ can be similar or dissimilar and are either hydrogen, alkyl (preferably of from 1–6 carbon atoms), aralkyl (preferably benzyl or phenethyl), alkenyl, alkynyl, and can be joined together through an atom of nitrogen, oxygen or sulfur to form a heterocyclic ring of from 5–6 atoms (such as imidazolinyl, piperidyl, pyrrolidinyl, morpholinyl, thiomorpholinyl or loweralkyl piperazinyl);
X and X' are selected from the group consisting of hydrogen, halogen (chlorine or fluorine), alkyl (preferably of from 1–6 carbon atoms), alkoxy (preferably of from 1–5 carbon atoms), perfluoroalkyl (e.g., trifluoromethyl), alkylmercapto (preferably of from 1–6 carbon atoms), alkylsulfonyl (preferably of from 1–6 carbon atoms), and dialkylsulfamoyl (preferably of from 2–8 carbon atoms);
m is an integer selected from the group consisting of 0 to 4 inclusive.

In accordance with the process of my invention, an acid halide of formula I is converted by treatment with ammonia or a primary or secondary amine to produce the corresponding amide or N-substituted amide of formula II. In carrying out this reaction, the acid halide is contacted in solution with an excess of the selected amine or ammonia preferably dissolved in a solvent for the reactants at room temperature of 25° C. and heated to the reflux temperature of the reaction mixture for a period of 1 to 5 hours. The amide which is formed is conveniently isolated by crystallization from the reaction mixture. Solvents which may be employed for carrying out this amidation reaction include the lower alkanols, e.g., ethanol, methanol, propanol, isopropanol, aromatic hydrocarbons such as benzene, toluene, xylene, high boiling tertiary amines such as pyridine, collidine and the like or mixtures of the above solvents with each other and/or with water.

In this manner there are produced amide intermediates, in our process of preparing arylthioaralkylamine, wherein the amide nitrogen is unsubstituted or substituted by one or more alkyl substituents or wherein the amide nitrogen forms part of a heterocyclic ring such as a piperidyl, pyrrolidinyl, morpholinyl, thiomorpholinyl, or 1-lower alkyl-4-piperazinyl ring.

The thus obtained arylthioaralkylamide or N-substituted amide II is then reduced to form the corresponding arylthioaralkylamine, e.g., 2-phenylthiobenzylamine, 3-phenylthiobenzylamine, 4-phenylthiobenzylamine, the corresponding N-substituted benzylamine, i.e., the N-alkyl or the N,N-dialkyl or the N-heterocyclic substituted compound. The reduction is readily effected by contacting the benzamide compound with lithium aluminum hydride in the presence of a suitable inert organic solvent, such as tetrahydrofuran, ether or other solvents conventionally employed with lithium aluminum hydride. Preferably, this reduction is carried out in the presence of aluminum chloride and an ether compatible with aluminum chloride as a solvent. The temperature at which the reduction is carried out is not critical but it is preferred to employ ambient temperatures and a range of from 0°–50° C. is satisfactory. The resulting benzylamine compound is readily recovered employing conventional techniques.

The arylthioaralkylamine, e.g., phenylthiobenzylamine, or the corresponding N-alkyl derivative thereof is readily converted to the corresponding lower aliphatic amide by reaction with an amide forming reagent. Thus the benzylamine compound or the corresponding N-substituted benzylamine compound is contacted, for example, with methyl formate or a lower alkanoyl halide such as acetyl chloride, propionyl chloride, butyryl chloride, or valeryl chloride to produce the corresponding N-substituted amide.

The amide obtained in the above manner is readily reduced with lithium aluminum hydride in the manner described for similar amides in the foregoing description, i.e., by reduction to the corresponding secondary or tertiary arylthiobenzylamine.

The starting 2, 3, or 4 phenylthiobenzoyl halide containing additional X and or X′ substituents are either known compounds or may be prepared from the corresponding phenylthiobenzoic acids by treatment with thionyl chloride or bromide.

EXAMPLE 1

N-Methyl-2-(phenylthio)-benzamide 2-(Phenylthio)benzoic acid, 15 g. (0.065 mole), together with 45 ml. of thionyl chloride and 200 ml. of dry benzene is stirred and heated to refluxing for about 16 hours. Solvent and excess thionyl chloride are evaporated under reduced pressure and the residue is freed from the last traces of thionyl chloride by the twice repeated addition of dry benzene and evaporation under reduced pressure. The residual oily acid chloride is dissolved in 50 ml. of acetone and the solution added dropwise with stirring to 98 ml. of 40% aqueous methylamine—25 ml. of water. The mixture is heated to refluxing for 3 hours. On cooling, the product crystallizes and is collected and washed with water; m.p. 102°–104° C. Repeated recrystallizations from ethyl acetate — hexane afford purified material, m.p. 105.5°–106.5° C.

Anal. Calc'd. for $C_{14}H_{13}NOS$: C, 69.10; H, 5.39; N, 5.76. Found: C, 68.95; H, 5.26; N, 5.57.

The above procedure is repeated employing in place of the methylamine starting material a stoichiometrically equivalent amount of ethylamine, propylamine, isopropylamine, n-butylamine, n-hexylamine, piperidine, morpholine, thiomorpholine, 1-methyl piperazine and 1-ethyl piperazine with resultant production respectively of N-methyl-2-(phenylthio)benzamide, N-ethyl-2-(phenylthio)benzamide, N-propyl-2-(phenylthio)benzamide, N-isopropyl-2-(phenylthio)benzamide, N(n)-butyl-2-(phenylthio)benzamide, N(n)-hexyl-2-(phenylthio)benzamide, N-piperidyl-2-(phenylthio)benzamide, N-morpholinyl-2-(phenylthio)benzamide, N-thiomorpholinyl-2-(phenylthio)benzamide, N-(1-methyl-4-piperazinyl)-2-(phenylthio)benzamide and N-(1-ethyl-4-piperazinyl)-2-(phenylthio)benzamide.

EXAMPLE 2

N-Methyl-2-(phenylthio)benzylamine

Lithium aluminum hydride, 1.52 g. (0.04 mole), is weighed under nitrogen, transferred to a dry nitrogen-flushed reaction flask, and suspended in 50 ml. of absolute ether. A solution of 5.34 g. (0.04 mole) of aluminum chloride in 60 ml. of absolute ether is added dropwise. The mixture, containing a white precipitate, is stirred at room temperature while a solution of 4.87 g. (0.02 mole) of N-methyl-2-(phenylthio)benzamide in 1 l. of absolute ether is added dropwise. The mixture is stirred at reflux for about 18 hours. After cooling, hydrolysis is effected by the dropwise addition of 60 ml. of water. After decantation of the ethereal layer and washing of the gelatinous precipitate with boiling ether, the precipitate is suspended in 40 ml. of 40% aqueous sodium hydroxide and 200 ml. of water. The mixture is extracted repeatedly with ether-benzene (1:1). Evaporation of solvents under reduced pressure from the washed and dried organic extract leaves the product as the residual oil. The base is converted to the hydrogen maleate salt by treating an ethereal solution with a slight excess of maleic acid dissolved in absolute ethanol. The hydrogen maleate separates in white crystals, m.p. 121°–122.5° C. The melting point in unchanged upon further recrystallization.

Anal. Calc'd. for $C_{14}H_{15}NS.C_4H_4O_4$: C, 62.59; H, 5.54; N, 4.06. Found: C, 62.91; H, 5.54; N, 4.01.

The procedure of this example is repeated using as the arylthiobenzamide starting material in place of N-methyl-2-(phenylthio)benzamide stoichiometrically equivalent amounts of the amides produced in accordance with the second paragraph of Example 1 with resultant production of N-ethyl-2-(phenylthio)benzylamine, N-propyl-2-(phenylthio)benzylamine, N-isopropyl-2-(phenylthio)benzylamine, N(n)-butyl-2-(phenylthio)benzylamine, N(n)-hexyl-2-(phenylthio)benzylamine, N-piperidyl-2-(phenylthio)benzylamine, N-morpholinyl-2-(phenylthio)benzylamine, N-thiomorpholinyl-2-(phenylthio)benzylamine, N-(1-methyl-4-piperazinyl)-2-(phenylthio)benzylamine and N-(1-ethyl-4-piperazinyl)-2-(phenylthio)benzylamine.

EXAMPLE 3

2-(Phenylthio)benzamide

Following the procedure described in Example 1, 2-(phenylthio)benzoyl chloride is prepared from 0.065 mole of 2-(phenylthio)benzoic acid and excess thionyl chloride. A solution of the oily acid chloride in 50 ml. of acetone is added dropwise with stirring to 100 ml. of concentrated ammonium hydroxide. The mixture is heated to refluxing for 3 hours. On cooling, the product separates and is collected.

EXAMPLE 4

2-(phenylthio)benzylamine

By following essentially the same procedure described in Example 2 but substituting 2-(phenylthio)-benzamide for the N-methyl-2-(phenylthio)benzamide, there is obtained 2-(phenylthio)benzylamine.

EXAMPLE 5

N,N-Dimethyl-2-(phenylthio)benzamide

Following the procedure described in Example 1, 2-(phenylthio)benzoyl chloride is prepared from 0.065 mole of 2-(phenylthio)benzoic acid and excess thionyl chloride. A solution of the oily acid chloride in 50 ml. of benzene is added dropwise with stirring to a solution of 7 g. of dimethylamine in 50 ml. of benzene. The mixture is heated briefly to refluxing. Evaporation of the solvent under reduced pressure leaves N,N-dimethyl-2-(phenylthio)benzamide as the residue.

In similar manner, 2-(phenylthio)benzoyl chloride is reacted with stoichiometrically equivalent amounts of diethylamine, dipropylamine and diisopropylamine with resultant production of the corresponding N,N-diethyl-2-(phenylthio)benzamide, N,N-dipropyl-2-(phenylthio)benzamide and N,N-diisopropyl-2-(phenylthio)benzamide.

EXAMPLE 6

N,N-Dimethyl-2-(phenylthio)benzylamine

By following essentially the same procedure described in Example 2 but substituting N,N-dimethyl-2-(phenylthio)benzamide for the N-methyl-2-(phenylthio)benzamide, there is obtained N,N-dimethyl-2-(phenylthio)benzylamine.

We claim:

1. Compounds having the formula

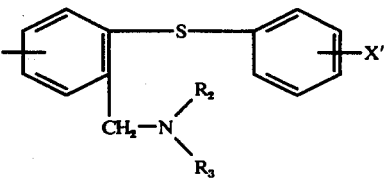

wherein $R_2$ and $R_3$ are independently selected from hydrogen, $C_1$–$C_6$ alkyl, $C_1$–$C_6$ alkenyl and $C_1$–$C_6$ alkynyl.

2. Compound of claim 1 wherein $R_2$ is hydrogen and $R_3$ is methyl.

3. Compounds of the formula wherein
  $R_2$ and $R_3$ are selected from the group consisting of hydrogen, $C_1$–$C_6$- alkyl, phenyl loweralkyl $C_2$–$C_6$- alkenyl and $C_2$–$C_6$ alkynyl; and
  X and X' are selected from the group consisting of hydrogen, halogen, alkyl, alkoxy, perfluoroalkyl, alkylmercapto and alkylsulfony; and non-toxic, pharmacologically acceptable salts thereof.

* * * * *